United States Patent
Seymour

(10) Patent No.: US 7,356,418 B2
(45) Date of Patent: Apr. 8, 2008

(54) SCIENTIST DOMAIN-CENTRIC USER INTERFACE AND ENABLING "SOFT" TRANSLATION

(75) Inventor: Sean L. Seymour, El Cerrito, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 11/480,214

(22) Filed: Jun. 30, 2006

(65) Prior Publication Data

US 2007/0016379 A1    Jan. 18, 2007

Related U.S. Application Data

(60) Provisional application No. 60/710,379, filed on Aug. 23, 2005, provisional application No. 60/696,077, filed on Jun. 30, 2005.

(51) Int. Cl.
*G01N 33/00* (2006.01)
*G06F 19/00* (2006.01)

(52) U.S. Cl. ........................................ 702/19

(58) Field of Classification Search ................... 702/19
See application file for complete search history.

(56) References Cited

U.S. PATENT DOCUMENTS

2003/0200032 A1 * 10/2003 Keating et al. ............... 702/19

* cited by examiner

*Primary Examiner*—Michael P. Nghiem
*Assistant Examiner*—Cindy D. Khuu
(74) *Attorney, Agent, or Firm*—Harness, Dickey & Pierce, P.L.C.

(57) ABSTRACT

The scientist domain-centric user interface system may prompt the user to supply scientist-centric information expressed utilizing terminology of a scientific domain, such as biology or analytical chemistry. A translation system then generates control parameters to control the search algorithm, thus relieving the user from having to learn how select and configure the algorithm control parameters directly.

36 Claims, 4 Drawing Sheets

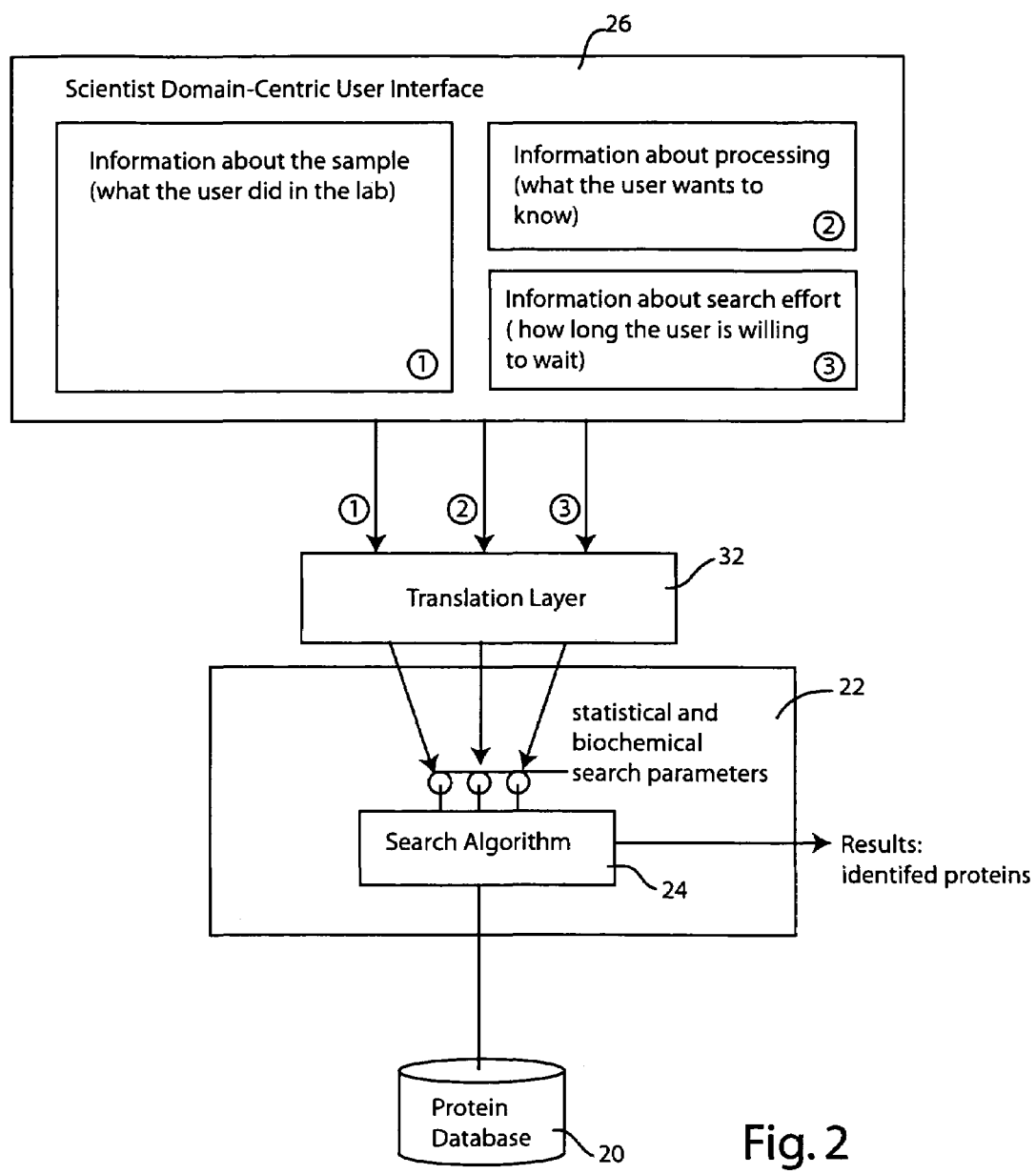

Fig. 3

Method: Standard method - EColi Project | Delete

Describe Sample

- Sample Type: Identification
- Cys Alkylation: Iodoacetamide
- Digestion: Trypsin
- Instrument: QSTAR ESI
- Special Factors:
  - ☐ Phosphorylation emphasis
  - ☐ Gel-based ID
  - ☒ Urea denaturation
- Species: Escherichia coli

Specify Processing

- ☐ Quantitate
- ID Focus:
  - ☒ Biological modifications
  - ☒ Amino acid substitutions
  - ☐ User-defined modifications
- Database: combined_KBMS5.0.20050302

Search Effort
- ○ Rapid ID
- ⊙ Thorough ID

Detected Protein Threshold [Unused ProtScore (Conf)]>: 2.0 (99.0%)

Save | Save As... | Cancel

SCIENTIST DOMAIN-CENTRIC USER INTERFACE AND ENABLING "SOFT" TRANSLATION

CROSS-REFERENCE TO RELATED APPLICATIONS

This application claims the benefit of U.S. Provisional Application No. 60/696,077, filed on Jun. 30, 2005, and U.S. Provisional Application No. 60/710,379, filed on Aug. 23, 2005. The disclosure of the above applications is incorporated herein by reference.

INTRODUCTION

Mass spectrometry is one of the major analytical techniques for identification of proteins and for conducting other life sciences experiments. Mass spectrometry instruments produce data that can be quite complex, often requiring sophisticated software to analyze the raw mass spectral data. Current industry standard software employ complex and somewhat arcane parameters that are not well understood by scientists working in the laboratory.

SUMMARY

As more fully set forth herein, a scientist domain-centric user interface system may prompt the user to supply scientist-centric information expressed utilizing terminology of a scientific domain, such as biology or analytical chemistry. A translation system then generates control parameters to control the search algorithm, thus relieving the user from having to learn how select and configure the algorithm control parameters directly.

These and other features of the present teachings are set forth herein. Further areas of applicability will become apparent from the description provided herein. It should be understood that the description and specific examples are intended for purposes of illustration only and are not intended to limit the scope of the present disclosure.

DRAWINGS

The skilled artisan will understand that the drawings, described below, and the XLM file listings provided in the Appendices, are for illustration purposes only. The drawings and listings are not intended to limit the scope of the present teachings in any way.

FIG. 2 is a software block diagram illustrating user interface and translation mechanisms may be configured to interact with the search algorithm of an informatics search tool;

FIG. 3 is an exemplary user interface; and

DETAILED DESCRIPTION

Figure 1:
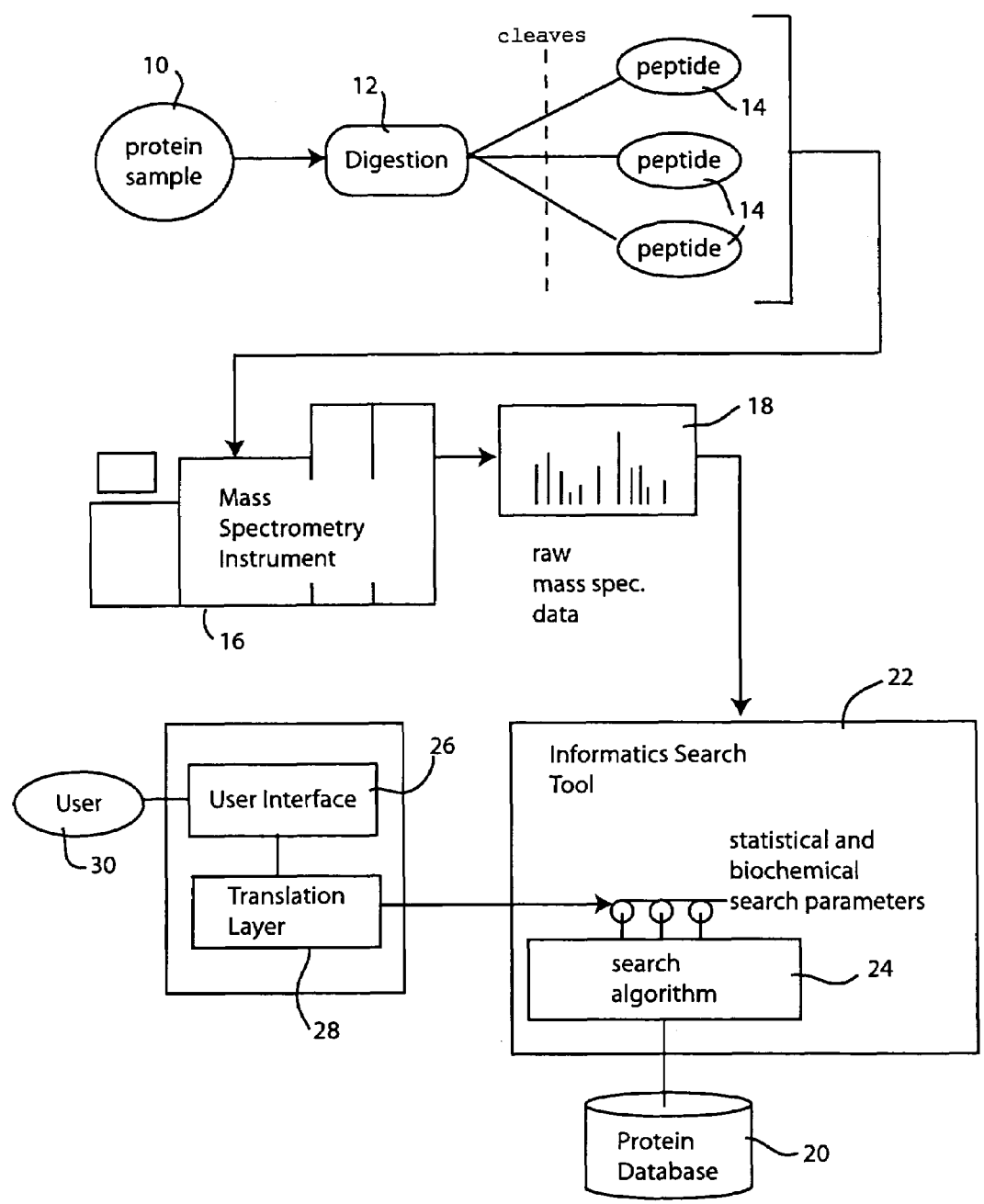
FIG. 1 is an exemplary workflow useful in understanding how the scientist domain-centric user interface and enabling "soft" translation mechanisms may be integrated into the workflow.

The following description is merely exemplary in nature and is not intended to limit the present disclosure, application, or uses. It should be understood that throughout the drawings, corresponding reference numerals indicate like or corresponding parts and features.

One of the main workflows currently used is the digestion of a protein sample with a reagent, which cleaves the full proteins into smaller peptides that are then easier to identify. Thus for illustration purposes, an exemplary workflow involving digestion of a protein sample has been illustrated in FIG. 1. It will be understood that this example is being provided to illustrate how the scientist domain-centric user interface an enabling "soft" translation mechanism might be used to perform mass spectrometry analysis. The user interface and translation techniques described here may be readily employed in other types of workflows.

For example, the user interface and translation techniques described herein might be applied in a workflow that looks at endogenously occurring peptides (ones that are isolated from natural in vivo digestion, rather than the result of intentional digestion as part of a workflow). Also, while the exemplary workflow illustrated in FIG. 1 accesses a database, these techniques may also be applied in applications that do not search a database for identification of biomolecules. Moreover, the techniques described herein may also be applied in applications that identify and quantify other biomolecules, such as metabolites and nucleic acids.

Referring to FIG. 1, the protein sample 10 is processed by digestion at 12, resulting in the protein being cleaved into a set of smaller peptides 14. These peptides are then processed through the mass spectrometry instrument 16 to generate raw mass spectrometry data, shown diagrammatically at 18. One objective of the mass spectrometry analytics is to find instances where the raw mass spectrometry data matches previously compiled proteomics data, such as may be stored in a protein database 20. Generally speaking, the task of finding matches (or partial matches) between the raw mass spectrometry data and the protein database requires a high degree of skill and specific knowledge of bioinformatics, statistics, molecular biology and chemistry, as well as knowledge of how peptides behave when processed through a mass spectrometry instrument. The current approach is to use an informatics search tool 22 to process the raw mass spectrometry data and then find matches in the protein database 20 based on the particular searching requirements specified by the user. The typical bioinformatics search tool will thus employ one or more search algorithms 24 to perform pattern matching searching operations and other data manipulations to identify candidate matches in the protein database.

Because of the sophistication of the pattern matching problem, and because of the highly complex nature of the raw mass spectrometry data, present day search algorithms require the user to make a number of parameter settings before the search algorithm is invoked. While some of the search parameters may be familiar to the typical user, unfortunately many are arcane. Thus, with conventional informatics search tools the user needs a great deal of experience, familiarity with current informatics publications describing the use of these tools, as well as a reasonable high mathematical and statistical skill level, and outright experimentation with the tools in order to know the optimal search parameter settings for a given experiment. This has, unfortunately, placed the use of mass spectrometry instruments and informatics search tools beyond the reach of many good biologists who would use these tools for protein research.

To solve this problem, the scientist domain-centric user interface and enabling "soft" translation system provides a specially designed user interface 26 and an associated translation layer 28 that allows the user 30 to set the search parameters for the search algorithm 24 without having any special knowledge of the informatics search tool as would conventionally be required. As will be more fully described, the user interface provides controls for protein identification software that have no parameters that would not be well understood by a novice user. This is accomplished by configuring the user interface to be in the language of the scientists' domain, with the translation layer 28 converting the user's instructions into the language of the search algorithm domain.

Referring to FIG. 2, an exemplary user interface is depicted at 26. The user interface is designed to be free of "arbitrary" parameters. Here we define an arbitrary parameter as one that impacts the quality of results obtained by the search algorithm, but where the optimal setting of the parameter is not readily appreciated or understood by the average scientist user. By way of example, many of the conventional search algorithms used to interpret mass spectrometry data include a search parameter used to constrain the number of missing cleavages with respect to a specified expected digestion pattern. A bioinformatics expert who is well-versed in the nuances of the informatics search tool would know that a setting of one or two is usually sufficient, but a novice has no reason to set these optimal values and instead might choose a value of five or fifteen. The novice having thus selected an arbitrary value that is far from optimal, because he or she does not know any better, will not obtain useful results. By presenting the user with a parameter that is not understood, the conventional informatics search tool invites the user to make arbitrary settings that can have quite a detrimental impact on whether usable results are obtained.

Another example of a parameter that would invite arbitrary settings involves the complicated issue of setting mass tolerances for database search methods. An expert would have a statistical sense of what effect the MS and the MS/MS tolerance will have on discrimination, false negatives, and search time, and the expert will also appreciate how to take into consideration the particular qualities of the instrument that produced the data. Unfortunately, the average scientist performing biological research would have no understanding of these issues and would thus need to resort to a great deal of experimentation in order to finally arrive at the optimal settings for a given type of data.

The user interface 26 (FIG. 2) provides a scientist domain-centric view that asks for three basic types of information: (1) information about the sample (i.e., what the user did in the lab); (2) information about processing (i.e., what the user wants to know); and (3) information about search effort (how long the user is willing to wait to receive results). These three different classes of information are fed through a translation layer 32 which generates the correct statistical and biochemical search parameters needed to initialize the search algorithm 24. The translation layer 32 embeds a great deal of search algorithm domain-specific knowledge so that the user does not need to be well-versed in the technical details of how to use the search algorithm.

FIG. 3 shows an exemplary scientist domain-centered user interface 26 in greater detail. As illustrated, the interface includes drop-down lists and check-boxes through which the user can provide information about the sample (what the user did in the lab). These are set forth in the region labeled "Describe Sample" and include the following topics: Sample Type; Cys Alkylation; Digestion; Instrument; Special Factors; and Species. For illustration purposes, some exemplary values have been selected in the associated drop-down lists and check-boxes.

Similarly, user interface 26 includes a region where the user can supply information about processing (what the user wants to know). These topics are set forth in the area designated "Special Processing" and include the following: Quantitate; ID Focus; Database. Again, exemplary selections have been made for illustration purposes.

Finally, the user interface 26 includes information about search effort (how long the user is willing to wait). This topic is presented under the label "Search Effort". The user can select by radio button either a rapid ID or a thorough ID. In addition, the user can employ a drop-down list to select what the detected protein threshold or confidence score should be. For illustration purposes here, the interface shows that a thorough ID has been selected and that a detected protein threshold of 2.0 (99.0%) has been chosen. The user can make the desired selections in interface 26 and then click the save, save as, or cancel buttons to save the settings for future use or to abort the process by cancelling. The user can select an appropriate name for his or her project which is displayed in the drop-down field 36. In this regard, the save as button would be used when the user wants to create a new name for the workflow or method, which would then appear as one of the choices when the drop-down list 36 is selected. A delete button 38 is also included to allow the user to quickly delete all settings and thus revert to an initialized or blank user interface screen.

In one embodiment of the scientist domain-centric user interface and enabling "soft" translation system a set of business rules can be employed to populate the user interface 26 with its drop-down list and check-box title descriptors and the associated user selectable choices. In one embodiment these business process rules can be expressed using XML files. As will be more fully discussed, these XML files also serve as the instructions by which the translation layer 32 (FIG. 2) generates statistical and biochemical search parameters for the search algorithm 24 based on the user's scientist domain instructions.

Figure 4:
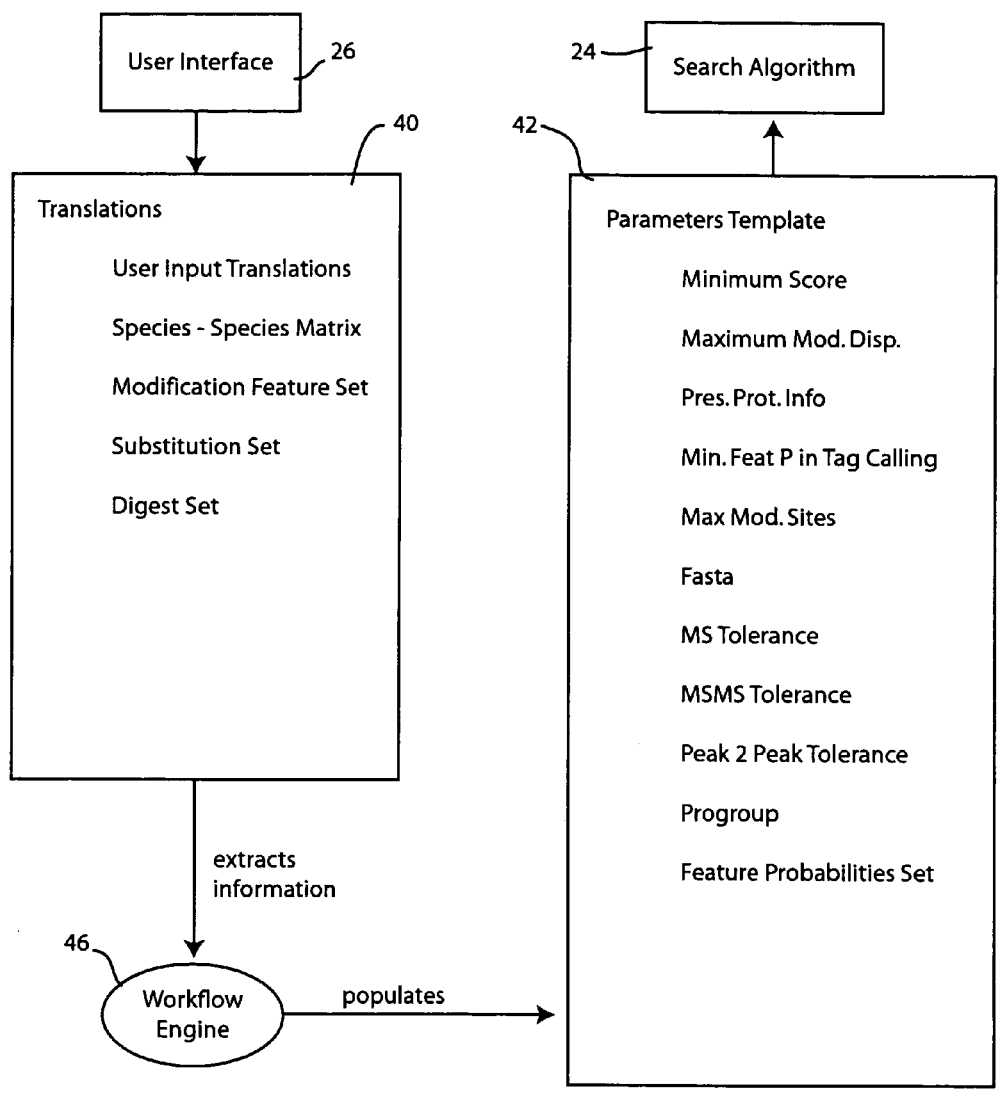
FIG. 4 is a block diagram illustrating an exemplary parameter translation system usable in the translation layer.

FIG. 4 represents a high level view showing how the translations file and a parameters template file (both expressed as XML files) may be structured to construct one implementation of the translation system. Translation file 40 maps onto user-selectable choices expressed in the terminology of the scientific domain for mediating user selection (e.g., fields in the user interface 26) while the parameter template file 42 maps onto algorithm control parameters used by the search algorithm 24. Exemplary XML files are appended to this application to further illustrate how one embodiment of the translation system may be configured. The XML file designated as "Appendix A" corresponds to the Translations file 40 of FIG. 4. The XML file designated as "Appendix B" corresponds to the Parameters Template file 42 of FIG. 4.

As shown in FIG. 4, a workflow engine 46 extracts information (user selection information mediated by the translations file) and then populates the parameters template file, based on the user selection information extracted. With reference to Appendix A, one can see that the translations file may contain a set of User Input Translations, that are hierarchically arranged to list the names of each of the user input fields (drop down lists, check boxes, radio buttons and the like). By making choices in the user interface 26, the user selects the desired value. Note that the input field names and the available choices are expressed utilizing terminology of a scientific domain, such as biology and/or analytical chemistry.

Some of the user selections can invoke further selections that the workflow engine is able to make automatically by following the hierarchical information expressed in the translations file. For example, see the user choice identified by the name "Special Factors," which appears as one of the choices under the User Input Translations heading. When the user chooses one of the special factors (also expressed in terminology of the scientific domain) the workflow engine is given a Mod Feature Set value, which the workflow engine can then look up in the Mod Feature Set section of the Translations file. For example, if the user selects "Urea Denaturation" the workflow engine can look up the associated value "Mod Feature Set:12." This, in turn, allows the workflow engine to jump to the section of the Translations file where Mod Feature Set:12 is described. For convenience, the parameters corresponding to Mod Feature Set:12 are set forth below:

```
<MOD_FEATURE_SET xml:id="MOD_FEATURE_SET:12" name="Urea denaturation treatment">
    <MOD_FEATURE mod="Protein Terminal Carbamyl">
        <OCCURRENCE target=" " term_spec="ProtNTerm" prob="0.2"/>
    </MOD_FEATURE>
    <MOD_FEATURE mod="Terminal Carbamyl">
        <OCCURRENCE target=" " term_spec="PepNTerm" prob="0.1"/>
    </MOD_FEATURE>
    <MOD_FEATURE mod="Carbamyl">
        <OCCURRENCE target="Lysine" prob="0.1"/>
        <OCCURRENCE target="Cysteine" prob="0.002"/>
        <OCCURRENCE target="Arginine" prob="0.1"/>
    </MOD_FEATURE>
    <MOD_FEATURE mod="Ornithine (from Arginine)">
        <OCCURRENCE target="Arginine" prob="0.05"/>
    </MOD_FEATURE>
</MOD_FEATURE_SET>
```

It can be seen from the above example, that a single selection of "Urea Denaturation" by the user can generate a potentially quite complex set of data that the workflow engine can then extract and use to populate the Parameters Template file. Also note in the above example that many of the data values are expressed as probabilities (prob="0.1", prob="0.002", etc.). The use of probabilistic values (expressing probabilistic rules) allows the workflow engine to populate the Parameters Template file with selected maximum and minimum ranges that, when supplied as parameters to the search algorithm, instruct the algorithm to control the search effort rapidity. Thus, if the user selects "Rapid ID" in the Search Effort portion of the user interface 26, the workflow engine can use these probability values to determine, a priori, what to ask the search algorithm to look for. By appropriate selection of values in the Parameters Template, the search algorithm can be controlled to perform exhaustive searches, or less exhaustive searches where some of the possible search paths are pruned or suppressed as the search proceeds.

By expressing the business logic or business rules in the form of hierarchical XML files, the embodiment illustrated in FIG. 4 and in the Appendices, has the advantage of allowing users to configure the system easily. With minimal knowledge of search engines, a user can examine the existing XML files and readily see how to add, delete or change information by simply mimicking what is already shown. For example, if a user wishes to add a new entry to the Digestion Set, it is a relatively simple matter to duplicate one of the existing entries and then edit the terms in the duplicate entry to define a new entry. The user is able to do this because the terms are expressed in the language of the scientific domain, which the user is already familiar with.

From the foregoing, it will be appreciated that the scientific domain-centric user interface and associated "soft" translation system removes much of the complexity and chances for making arbitrary, counterproductive parameter settings. Thus the user is no longer confronted with making arcane decisions about algorithm control parameters, such as mass tolerances, the number of missed cleavages allowed, selection of specific modifications and/or mutations, and subtopics. Instead, the user simply enters information that he or she readily knows, about what the user did in the lab, what the user wants to know from the analysis and how long the user is willing to wait for results (whether high accuracy, long search time is appropriate or whether a lower accuracy, fast answer is acceptable).

What is claimed is:

1. A scientist-centric interface system for conducting research using a mass spectrometry instrument with an informatics search tool that utilizes a search algorithm to identify biomolecules, the search algorithm having a set of predefined algorithm control parameters used to control how the search algorithm operates, comprising:

a user interface that prompts a user to supply scientist-centric information expressed utilizing terminology of a scientific domain selected from the domains of biology, analytical chemistry or any combination thereof;

a translation system receptive of said scientist-centric information and operative to generate control parameters selected from said set of predefined algorithm control parameters and said translation system having a search algorithm interface whereby said generated control parameters are supplied to said search algorithm to control how the algorithm operates; wherein said translation system includes:

a translation file that includes a set of hierarchically organized rules that map onto user-selectable choices expressed in the terminology of the scientific domain for mediating user selection;

a parameters template file that includes a set of rules that map onto the algorithm control parameters; and a workflow engine that extracts user selection information mediated by said translation file and populates the parameters template file based on the user selection information extracted.

2. The system of claim 1 wherein said user interface additionally prompts the user to supply information describing a desired search effort rapidity or thoroughness.

3. The system of claim 1 wherein the user interface prompts the user to supply scientist-centric information about a biological sample.

4. The system of claim 1 wherein the user interface prompts the user to supply scientist-centric information about steps performed on a biological sample prior to analysis by mass spectrometry.

5. The system of claim 1 wherein the user interface prompts the user to supply scientist-centric information about what the user wants to learn from the analysis by mass spectrometry.

6. The system of claim 1 wherein the set of predefined algorithm control parameters includes a parameter indicative of mass tolerance and wherein said translation system generates said mass tolerance parameter based on supplied scientist-centric information.

7. The system of claim 6 wherein said user interface does not prompt the user to explicitly supply said mass tolerance parameter.

8. The system of claim 1 wherein the set of predefined algorithm control parameters includes a parameter indicative of the number of missed cleavages allowed and wherein said translation system generates said number of allowed missed cleavages parameter based on supplied scientist-centric information.

9. The system of claim 8 wherein said user interface does not prompt the user to explicitly supply said number of allowed missed cleavages parameter.

10. The system of claim 1 wherein the set of predefined algorithm control parameters includes a parameter indicative of a selection of specific modifications and wherein said translation system generates said selection of specific modifications parameter based on supplied scientist-centric information.

11. The system of claim 10 wherein said user interface does not prompt the user to explicitly supply said selection of specific modifications parameters.

12. The system of claim 1 wherein the set of predefined algorithm control parameters includes a parameter indicative of a selection of specific mutations and wherein said translation system generates said selection of specific mutations parameter based on supplied scientist-centric information.

13. The system of claim 12 wherein said user interface does not prompt the user to explicitly supply said selection of specific mutations parameter.

14. The system of claim 1 wherein the set of predefined algorithm control parameters includes a parameter indicative of a subtopic and wherein said translation system generates said subtopic parameter based on supplied scientist-centric information.

15. The system of claim 14 wherein said user interface does not prompt the user to explicitly supply said subtopic parameter.

16. The system of claim 1 wherein the set of predefined algorithm control parameters includes a parameter indicative of a modification and wherein said translation system generates said modification parameter based on supplied scientist-centric information relating to cysteine alkylation reagent name.

17. The system of claim 16 wherein said user interface does not prompt the user to explicitly supply said modification parameter.

18. The system of claim 1 wherein the set of predefined algorithm control parameters includes a parameter indicative of an algorithmic taxonomy filter setting and wherein said translation system generates said algorithmic taxonomy filter setting parameter based on supplied scientist-centric information relating to species of a sample.

19. The system of claim 18 wherein said user interface does not prompt the user to explicitly supply said algorithmic taxonomy filter setting parameter.

20. The system of claim 1 wherein the set of predefined algorithm control parameters includes a parameter indicative of a digestion rule algorithmic setting and wherein said translation system generates said digestion rule algorithmic setting parameter based on supplied scientist-centric information relating to the actual digestion of a sample.

21. The system of claim 20 wherein said user interface does not prompt the user to explicitly supply said digestion rule algorithmic setting parameter.

22. The system of claim 1 wherein said translation system includes a set of rules that define parameter translations between terminology in the scientific domain and the algorithm control parameters.

23. The system of claim 22 wherein said set of rules comprises business rules expressed in xml files that are read by said translation system.

24. The system of claim 1 wherein said translation system includes a set of hierarchically organized rules that define parameter translations between terminology in the scientific domain and the algorithm control parameters.

25. A scientist-centric interface system for conducting research using a mass spectrometry instrument with an informatics search tool that utilizes a search algorithm to identify biomolecules, the search algorithm having a set of predefined algorithm control parameters used to control how the search algorithm operates, comprising:

a user interface that prompts a user to supply scientist-centric information expressed utilizing terminology of a scientific domain selected from the domains of biology, analytical chemistry or any combination thereof;

a translation system receptive of said scientist-centric information and operative to generate control parameters selected from said set of predefined algorithm control parameters and said translation system having a search algorithm interface whereby said generated control parameters are supplied to said search algorithm to control how the algorithm operates;

wherein said translation system includes a set of probabilistic rules that define parameter translations between terminology in the scientific domain and the algorithm control parameters.

26. The system of claim 1 wherein said translation system includes a set of rules stored in at least one user-editable file that define parameter translations between terminology in the scientific domain and the algorithm control parameters.

27. The system of claim 25 wherein the user interface prompts the user to supply scientist-centric information about steps performed on a biological sample prior to analysis by mass spectrometry.

28. The system of claim 25 wherein the user interface prompts the user to supply scientist-centric information about what the user wants to learn from the analysis by mass spectrometry.

29. The system of claim 25 wherein the set of predefined algorithm control parameters includes a parameter indicative of the number of missed cleavages allowed and wherein said translation system generates said number of allowed missed cleavages parameter based on supplied scientist-centric information.

30. The system of claim 25 wherein the set of predefined algorithm control parameters includes a parameter indicative of a modification and wherein said translation system generates said modification parameter based on supplied scientist-centric information relating to cysteine alkylation reagent name.

31. The system of claim 25 wherein the set of predefined algorithm control parameters includes a parameter indicative of a digestion rule algorithmic setting and wherein said translation system generates said digestion rule algorithmic setting parameter based on supplied scientist-centric information relating to the actual digestion of a sample.

32. The system of claim 25 wherein said translation system includes a set of rules that define parameter translations between terminology in the scientific domain and the algorithm control parameters.

33. The system of claim 32 wherein said set of rules comprises business rules expressed in xml files that are read by said translation system.

34. The system of claim 25 wherein said translation system includes a set of rules stored in at least one user-editable file that define parameter translations between terminology in the scientific domain and the algorithm control parameters.

35. A method for interacting with an informatics search tool utilizing a search algorithm to extract information from a protein database, the search algorithm having a set of predefined algorithm control parameters used to control how information from a protein database is extracted, comprising the steps of:

employing a user interface to prompt the user to supply scientist-centric information expressed utilizing terminology of a scientific domain selected from the domains of biology, analytical chemistry or any combination thereof;

using said supplied scientist-centric information to automatically generate control parameters selected from the set of predefined algorithm control parameters by a translation process, the translation process including:

mapping a first set of rules onto user selectable choices expressed in the terminology of the scientific domain for mediating user selection;

mapping a second set of rules onto the algorithm control parameters; and extracting user selection information mediated by the mapping of the first set of rules and populating the second set of rules mapped onto the algorithm control parameters in order to generate control parameters;

and supplying said generated control parameters to said search algorithm to control how information from the protein database is processed.

36. A method for interacting with an informatics search tool utilizing an algorithm to process information from a laboratory instrument, the algorithm having a set of predefined algorithm control parameters used to control how the instrument is controlled, comprising the steps of:

employing a user interface to prompt the user to supply scientist-centric information expressed utilizing terminology of a scientific domain selected from the domains of biology, analytical chemistry or any combination thereof;

using said supplied scientist-centric information to automatically generate control parameters selected from the set of predefined algorithm control parameters by a translation process, the translation process including:

mapping a first set of rules onto user selectable choices expressed in the terminology of the scientific domain for mediating user selection;

mapping a second set of rules onto the algorithm control parameters; and extracting user selection information mediated by the mapping of the first set of rules and populating the second set of rules mapped onto the algorithm control parameters in order to generate control parameters;

and supplying said generated control parameters to said algorithm to control how information from the laboratory instrument is processed.

* * * * *